(12) United States Patent
Cunliffe et al.

(10) Patent No.: US 12,419,723 B2
(45) Date of Patent: Sep. 23, 2025

(54) AUTOMATED PROCESS FOR INTERMEDIATE ORTHODONTIC DIGITAL SETUP REUSE DUE TO TREATMENT PLAN MODIFICATIONS

(71) Applicant: Solventum Intellectual Properties Company, Maplewood, MN (US)

(72) Inventors: Alexandra R. Cunliffe, St. Paul, MN (US); Guruprasad Somasundaram, Woodbury, MN (US); Benjamin D. Zimmer, Hudson, WI (US); Nitsan Ben-Gal Nguyen, Apple Valley, MN (US); Vera Shuman, St. Paul, MN (US); Nancy M. Amato, Champaign, IL (US); Shawna L. Thomas, College Station, TX (US)

(73) Assignee: Solventum Intellectual Properties Company, Maplewood, MN (US)

( * ) Notice: Subject to any disclaimer, the term of this patent is extended or adjusted under 35 U.S.C. 154(b) by 673 days.

(21) Appl. No.: 17/441,331

(22) PCT Filed: Mar. 31, 2020

(86) PCT No.: PCT/IB2020/053060
§ 371 (c)(1),
(2) Date: Sep. 21, 2021

(87) PCT Pub. No.: WO2020/202009
PCT Pub. Date: Oct. 8, 2020

(65) Prior Publication Data
US 2022/0160469 A1    May 26, 2022

Related U.S. Application Data

(60) Provisional application No. 62/829,065, filed on Apr. 4, 2019.

(51) Int. Cl.
*A61C 7/00*    (2006.01)
*G06T 5/70*    (2024.01)
(Continued)

(52) U.S. Cl.
CPC .............. *A61C 7/002* (2013.01); *G06T 5/70* (2024.01); *G16H 20/40* (2018.01); *G16H 30/40* (2018.01); *G06T 2207/30036* (2013.01)

(58) Field of Classification Search
CPC .......... A61C 7/002; A61C 7/00; G16H 30/40; G16H 20/40; G06T 5/70; G06T 2207/30036
(Continued)

(56) References Cited

U.S. PATENT DOCUMENTS 6,488,499 B1 * 12/2002 Miller ..................... A61C 7/08
                                                    433/24
6,602,070 B2    8/2003 Miller
(Continued)

FOREIGN PATENT DOCUMENTS

CN    101006940 A    8/2007
CN    101977564 A    2/2011
(Continued)

OTHER PUBLICATIONS

EESR, EP20782765.0, dated Nov. 30, 2022, 3 pages.
International Search report for PCT International Application No. PCT/IB2020/053060 mailed on Jul. 9, 2020, 9 pages.

*Primary Examiner* — Yogesh P Patel

(57) ABSTRACT

A method for generating and reusing digital setups for an orthodontic treatment path. The method receives a digital 3D model of teeth, optionally performs interproximal reduction on the model, and generates an initial treatment path with stages including an initial, final, and intermediate setups. The method divides the initial treatment path into initial steps of feasible motion of the teeth resulting in a final treatment path with setups corresponding with the initial steps. For a treatment redesign, the method computes new steps of feasible motion for only a portion of the initial treatment path and based upon the initial steps, and gener-
(Continued)

ates the final path with new setups corresponding with the new steps. The setups can be used to make orthodontic appliances, such as clear tray aligners.

16 Claims, 4 Drawing Sheets

(51) Int. Cl.
    *G16H 20/40*     (2018.01)
    *G16H 30/40*     (2018.01)

(58) Field of Classification Search
    USPC .......................................................... 433/24
    See application file for complete search history.

(56) References Cited

U.S. PATENT DOCUMENTS

| | | | |
|---|---|---|---|
| 6,783,360 B2 * | 8/2004 | Chishti | A61C 7/00 433/6 |
| 7,605,817 B2 | 10/2009 | Zhang | |
| 7,956,862 B2 | 6/2011 | Zhang | |
| 10,595,965 B2 * | 3/2020 | Khardekar | G06F 30/00 |
| 2002/0042038 A1 * | 4/2002 | Miller | G16H 50/50 433/215 |
| 2005/0048432 A1 * | 3/2005 | Choi | A61C 7/002 433/24 |
| 2007/0238065 A1 * | 10/2007 | Sherwood | A61C 7/08 433/24 |
| 2008/0057461 A1 * | 3/2008 | Cheng | A61C 7/00 433/24 |
| 2008/0248443 A1 | 10/2008 | Chishti et al. | |
| 2008/0306724 A1 * | 12/2008 | Kitching | A61C 7/00 704/2 |
| 2013/0309626 A1 * | 11/2013 | Arunachalam | A61C 7/28 433/24 |
| 2015/0351871 A1 * | 12/2015 | Chishti | A61C 7/002 425/150 |

FOREIGN PATENT DOCUMENTS

| | | |
|---|---|---|
| CN | 107530141 A | 1/2018 |
| CN | 109310488 A | 2/2019 |
| WO | 2019069191 A3 | 4/2019 |
| WO | WO 2019-069191 | 4/2019 |

* cited by examiner

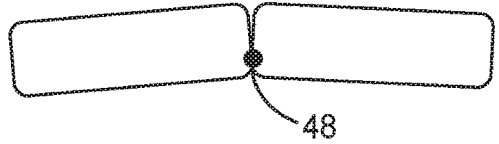
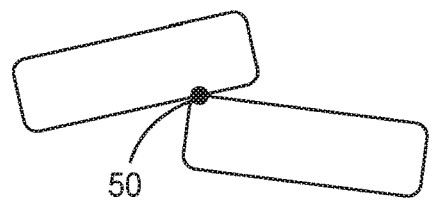
*Fig. 5A*  *Fig. 5B*
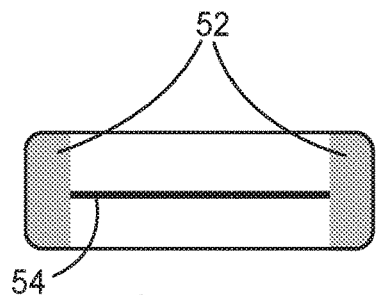
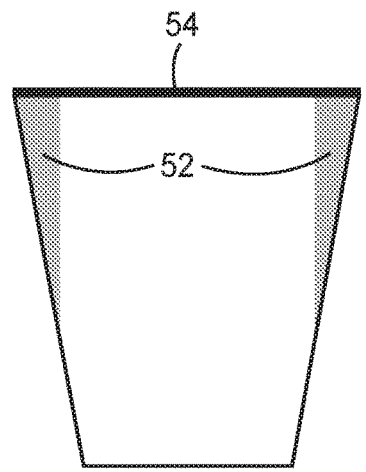
*Fig. 6A*  *Fig. 6B*
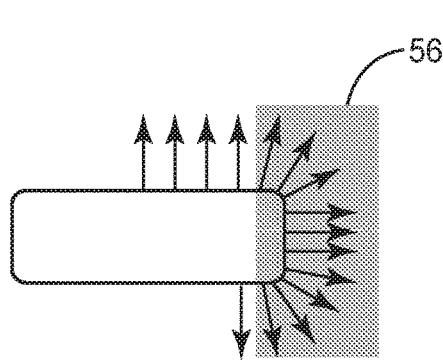
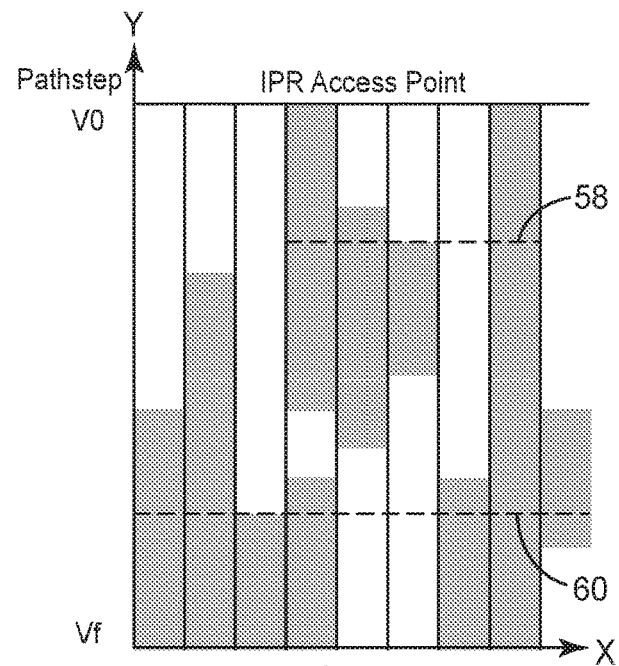
*Fig. 7*  *Fig. 8*

AUTOMATED PROCESS FOR INTERMEDIATE ORTHODONTIC DIGITAL SETUP REUSE DUE TO TREATMENT PLAN MODIFICATIONS

CROSS REFERENCE TO RELATED APPLICATIONS

This application is a national stage filing under 35 U.S.C. 371 of PCT/IB2020/053060, filed Mar. 31, 2020, which claims the benefit of U.S. Provisional Application No. 62/829,065, filed Apr. 4, 2019, the disclosures of which are incorporated by reference in their entireties herein.

BACKGROUND

Intermediate staging of teeth from a malocclusion stage to a final stage requires determining accurate individual teeth motions in a way that teeth are not colliding with each other, the teeth move toward their final state, and the teeth follow optimal (preferably short) trajectories. Since each tooth has 6 degrees-of-freedom and an average arch has about 14 teeth, finding the optimal teeth trajectory from initial to final stage has a large and complex search space. A need exists to simplify this optimization problem by dividing the trajectory to several shorter and easier-to-find trajectories and by reusing previous trajectories for treatment plan redesign.

SUMMARY

An embodiment includes a method for generating and reusing setups for an orthodontic treatment path to accommodate treatment path redesigns. The method includes receiving a digital 3D model of teeth and generating an initial treatment path with stages including an initial setup, a final setup, and a plurality of intermediate setups. The method also includes dividing the initial treatment path into initial steps of feasible motion of the teeth resulting in a final treatment path with setups corresponding with the initial steps. For a treatment redesign, the method further includes computing new steps of feasible motion of the teeth for only a portion of the initial treatment path and based upon the initial steps, and generating the final treatment path with new setups corresponding with the new steps.

BRIEF DESCRIPTION OF THE DRAWINGS

The accompanying drawings are incorporated in and constitute a part of this specification and, together with the description, explain the advantages and principles of the invention. In the drawings.

FIGS. 5A and 5B are diagrams illustrating accessible and inaccessible contacts for IPR application;

FIGS. 6A and 6B are diagrams illustrating IPR regions for accessible contact points;

FIG. 7 is a diagram illustrating an IPR region for accessible contact points; and FIG. 8 is a graph of an accessibility matrix for IPR.

DETAILED DESCRIPTION

Embodiments of this invention include a possibly partially to fully automated system to generate a set of intermediate orthodontic setups that allow a set of teeth to move from the maloccluded to the final setup state or allow for a partial treatment from one state to another state (e.g., an initial state to a particular intermediate state). Each arrangement of teeth ("state" or "setup") is represented as a node in a graph, and robotic motion planning is used to expand the graph and search for a path of valid states. These states or setups can be a digital representation of the arrangement of teeth at a particular stage of treatment, where the representation is a digital 3D model. The digital setups can be used, for example, to make orthodontic appliances such as clear tray aligners to move teeth along a treatment path. The clear tray aligners can be made by, for example, converting the digital setup into a corresponding physical model and thermoforming a sheet of material over the physical model or by 3D printing the aligner from the digital setup. Other orthodontic appliances, such as brackets and archwires, can also be configured based upon the digital setups.

The system and method can take into consideration interproximal reduction (IPR), which is the removal of some of the outer tooth surface, called enamel IPR is also known as, and the term IPR includes, slenderizing, stripping, enamel reduction, reproximation, and selective reduction. IPR can be used, for example, between teeth that touch in order to make room to move teeth in orthodontic procedures. The system and method apply IPR to a digital 3D model of teeth to simulate application of IPR to actual teeth represented by the model. In other embodiments, the system and method do not require consideration of IPR. In other embodiments, the system and method can model the opposite of IPR using the same or similar techniques, for example as applied to bridges or implants.

In one embodiment, the method: 1) performs IPR up-front on a digital 3D model of teeth and generates an initial treatment path with digital setups; 2) computes IPR accessibility for each tooth at each stage of the initial treatment path and possibly determines when to apply IPR; and 3) applies IPR throughout the treatment path and divides the treatment path into steps of biologically feasible motion, a trajectory with points for the digital setups to make appliances corresponding with each setup. In other embodiments, the method can proceed without IPR or with IPR when possible to perform IPR.

Figure 1:
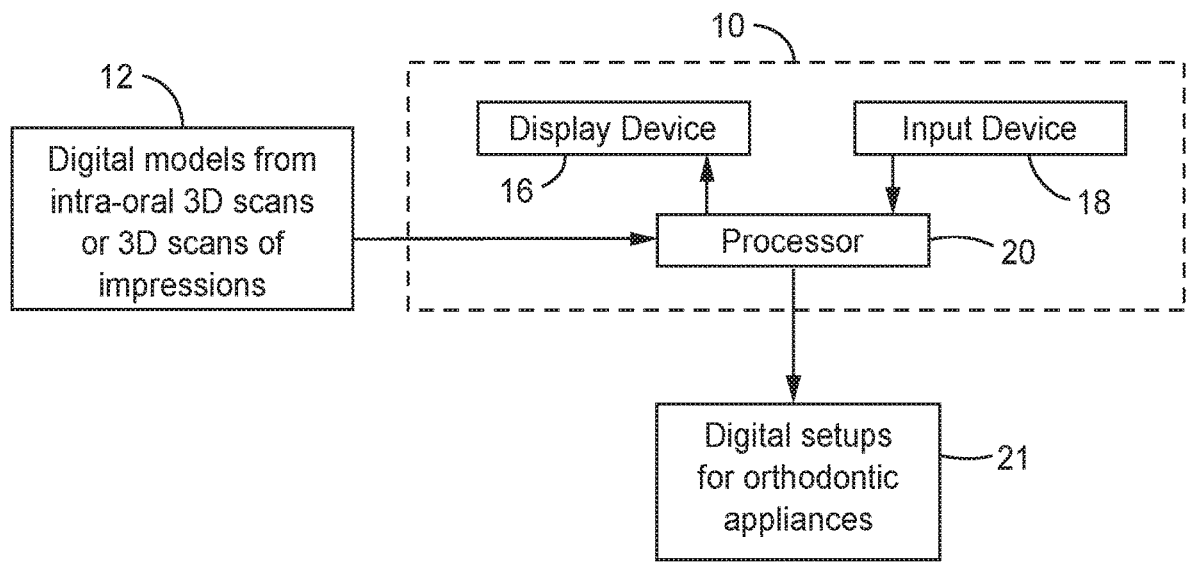
FIG. 1 is a diagram of a system for generating digital setups for orthodontic appliances.

FIG. 1 is a diagram of a system 10 for generating digital setups for orthodontic appliances (21). System 10 includes a processor 20 receiving digital 3D models of teeth (12) from intra-oral 3D scans or scans of impressions of teeth, or in other embodiments the system receives user manual input. System 10 can also include an electronic display device 16, such as a liquid crystal display (LCD) device, and an input device 18 for receiving user commands or other information. Systems to generate digital 3D images or models based upon image sets from multiple views are disclosed in U.S. Pat. Nos. 7,956,862 and 7,605,817, both of which are incorporated herein by reference as if fully set forth. These systems can use an intra-oral scanner to obtain digital images from multiple views of teeth or other intra-oral structures, and those digital images are processed to generate a digital 3D model representing the scanned teeth and gingiva. System 10 can be implemented with, for example, a desktop, notebook, or tablet computer. System 10 can receive the 3D scans locally or remotely via a network.

The 3D scans addressed herein are represented as triangular meshes. The triangular mesh is a common representation of 3D surfaces and has two components. The first component, referred to as the vertices of the mesh, are simply the coordinates of the 3D points that have been reconstructed on the surface—i.e., a point cloud. The second component, the mesh faces, encodes the connections between points on the object and is an efficient way of interpolating between the discrete sample points on the continuous surface. Each face is a triangle defined by three vertices, resulting in a surface that can be represented as a set of small triangular planar patches.

A. Algorithm Overview

Embodiments include a motion planning-based approach to generate intermediate setups (staging) given an initial maloccluded setup and a final proposed setup. The goal is to produce a series of setups that bring the maloccluded setup into the final proposed setup that also meet some evaluation criteria while satisfying per-stage tooth movement limits. Evaluation criteria may require collision-free setups, minimal gingiva displacement, permitted motion, how motion can be related, or other conditions.

Figure 2:
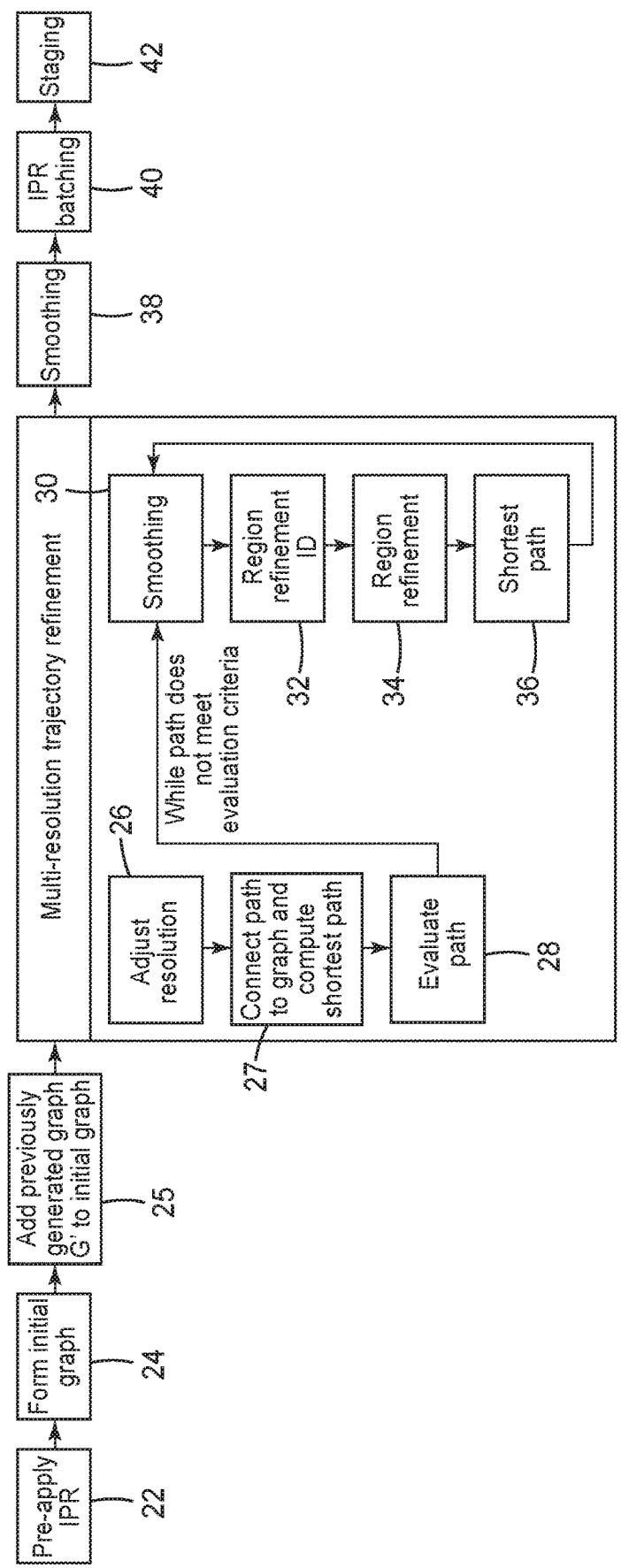
FIG. 2 is a flow chart of a method for generating digital setups for orthodontic appliances.

The flow chart shown in FIG. 2 provides an overview of the system and method. A sequence of key setups is provided as input, where the first is the maloccluded state, the last is the final proposed setup, and the others are additional setups ("key setups") that will help guide the motion. Key setups are a way to guide the search for intermediate setups, but key setups are not required for intermediates. For example with key setups, when creating space to reduce the crowding of teeth, trajectories often should move and tip the teeth outward, apply IPR, and then retract/upright the teeth. In this case, one key setup could be added in addition to the first and last that specifies this flared-out configuration. Intermediate key setups may be generated manually by a technician or through an automated approach. One potential method for intermediate key setup generation is to encode a rule for coordinated tooth motion (e.g., flare out) that can be applied to a set of teeth. Another possible method uses a logic controller to create key intermediate setups based upon inputs, outputs, and rules as specified below.

The input variables of this logic controller are:

The difference between the current and the target position (i.e. position error vector) for each tooth ($e_x$, $e_y$, $e_z$), The Euler angles error vector for each tooth ($e_\varphi$, $e_\theta$, $e_\psi$), The penetration depth for tooth collision (Pd), and The direction of a possible penetration for tooth collision ($c_x$, $c_y$, $c_z$).

The output variables or the control commands of this logic controller are:

The Euler angles vector of the rotation command for each tooth ($d_\varphi$, $d_\theta$, $d_\omega$), and The translation vector command for each tooth ($d_x$, $d_y$, $d_z$).

In one embodiment, there are two sets of control rules that govern the key frame generation system: to control each tooth to converge to the tooth's final state or an intermediate state (Table 1), and to avoid collisions by moving in the opposite direction of the penetration depth (Table 2).

TABLE 1

A subset of rules that are applied to move a tooth along the x-axis when the tooth is free to move (i.e. moving toward the target position will not increase the penetration depth)

IF ((Pd is ZERO) OR ($c_x$ is ZERO) OR ($c_x$ is NEGATIVE)) AND ($e_x$ is POSITIVE) THEN $d_x$ is POSITIVE.
IF ((Pd is ZERO) OR ($c_x$ is ZERO) OR ($c_x$ is POSITIVE)) AND ($e_x$ is NEGATIVE) THEN $d_x$ is NEGATIVE.
IF ((Pd is ZERO) OR ($c_x$ is ZERO)) AND ($e_x$ is ZERO) THEN $d_x$ is ZERO.
. . .

TABLE 2

A subset of rules that are applied to move a tooth along the x-axis when the tooth is not free to move (i.e. moving toward the target position will increase the penetration depth).

IF (Pd is SMALL) AND ($c_x$ is POSITIVE) AND ($e_x$ is POSITIVE) THEN $d_x$ is ZERO.
IF (Pd is LARGE) AND ($c_x$ is POSITIVE) AND ($e_x$ is POSITIVE) THEN $d_x$ is NEGATIVE.
IF (Pd is SMALL) AND ($c_x$ is POSITIVE) AND ($e_x$ is ZERO) THEN $d_x$ is ZERO.
IF (Pd is LARGE) AND ($c_x$ is POSITIVE) AND ($e_x$ is ZERO) THEN $d_x$ is NEGATIVE.
IF (Pd is SMALL) AND ($c_x$ is NEGATIVE) AND ($e_x$ is ZERO) THEN $d_x$ is ZERO.
IF (Pd is LARGE) AND ($c_x$ is NEGATIVE) AND ($e_x$ is ZERO) THEN $d_x$ is POSITIVE.
IF (Pd is SMALL) AND ($c_x$ is NEGATIVE) AND ($e_x$ is NEGATIVE) THEN $d_x$ is ZERO.
IF (Pd is LARGE) AND ($c_x$ is NEGATIVE) AND ($e_x$ is NEGATIVE) THEN $d_x$ is POSITIVE.
. . .

Figure 3:
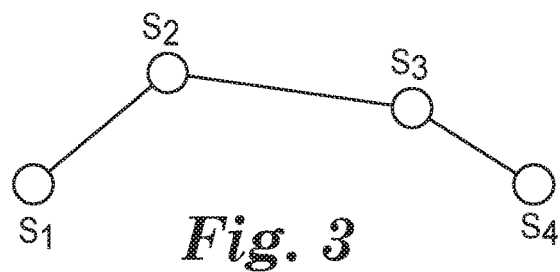
FIG. 3 is a graph illustrating an initial sequence of digital setups.

All IPR is pre-applied to the maloccluded state (step 22). This means that the total IPR prescribed to be performed by the end of treatment is applied to the geometry that will be used throughout the region refinement step. After IPR is applied, a graph is formed including the key setups, $S_1$, $S_2$, $S_3$, and $S_4$ (step 24) as shown in FIG. 3, where $S_1$ is the initial maloccluded state, $S_4$ is the final setup at the end of treatment, and $S_2$ and $S_3$ are intermediate setups at different stages of treatment. Once a sequence of states has been created, multi-resolution trajectory refinement is performed (steps 26, 28, 30, 32, 34, and 36 explained below).

Figure 4A:
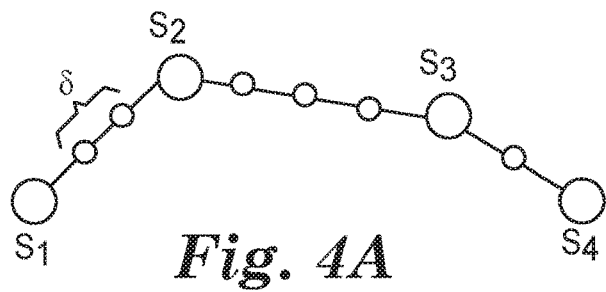
FIGS. 4A-4D are graphs illustrating trajectory refinement for a sequence of digital setups.
Figure 4B:
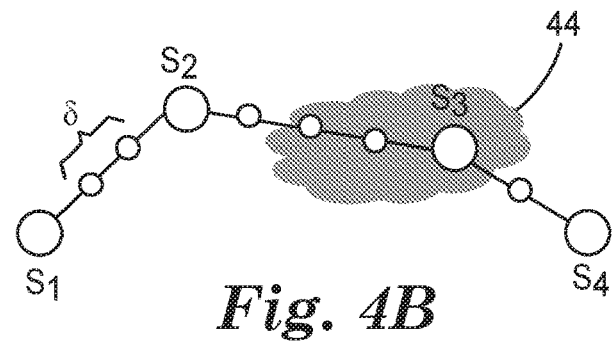
Figure 4C:
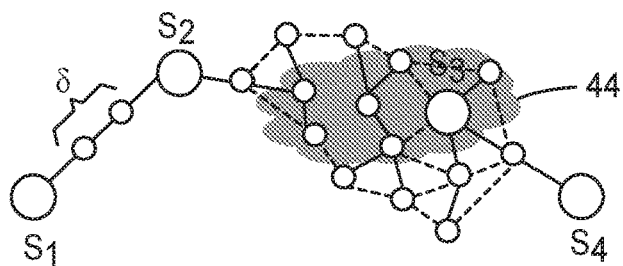
Figure 4D:
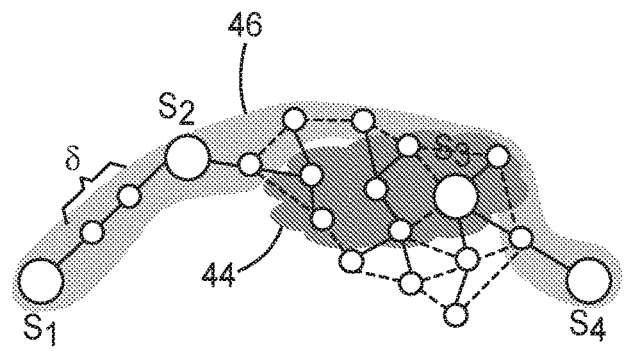

This trajectory refinement process is described for a single resolution in FIGS. 4A-4D. First, the shortest path through the graph is linearly interpolated at a resolution δ (FIG. 4A), where δ changes at each resolution in the multi-resolution approach. Once interpolated, each setup in the sequence is evaluated to see if the setup meets the given criteria (FIG. 4B). If the evaluation criteria are not met, the refinement process repeats until the shortest path meets the criteria. Invalid states are targeted for refinement (the setup in region 44 in FIG. 4C), and a search commences from these states and their neighbors. Here the search is at the same resolution δ for the linear interpolation. Additional edges are generated during the search (the dashed lines in FIGS. 4C and 4D) to allow for multiple paths in the graph between the initial and final setups. Edges are weighted by the node that they proceed from. After many new edges are added, a search is performed to find the new shortest path. If a path is found (region 46 in FIG. 4D), path smoothing can be performed. Path smoothing interpolates new edges between nearby states in the path and finds a new shortest path; edges are only added if the edges meet the given criteria at the resolution 6. In other embodiments, smoothing is not required. The refinement process repeats until all setups in the sequence meet the given criteria.

Once the sequence meets the evaluation criteria, the sequence is smoothed again (step 38), and a final path is returned (steps 40 and 42). The path is subsequently input into an IPR application step, which identifies where in the trajectory IPR application should occur. Staging then returns a series of setups at resolution l which may be larger than δ.

This process also incorporates treatment re-design features (steps 25 and 27).

Algorithm 1 details this entire process, except the treatment re-design features which are detailed below. Specific sub-algorithm designs are discussed afterward.

---
Algorithm 1
---

Input: The initial and final setups $v_0$ and $v_f$, and any key intermediate stages. Typically, $v_0$ is the maloccluded setup and $v_f$ is the final proposed setup.
Input: A list of step sizes, ResolutionList.
Input: A staging limit l
Input: An evaluation function E that assigns scores to setups.
Output: A staged trajectory at resolution l that starts at $v_0$, ends at $v_f$, and minimizes undesirable motions.
1. v0 ← PreapplyIPR($v_0$, $v_f$)
2. Form a graph G containing vertices $v_0$ and $v_f$. $v_0$ and $v_f$ are connected in G. This may simply be a graph with only these 2 vertices and a single edge connecting them, a graph with a series of key setups informed by the case's motion rules, or a graph from a prior setup proposal search.
3. P ← ShortestPath(G, $v_0$, $v_f$)
4. for δ in ResolutionList do
5.   P ← AdjustResolution(G, P, δ)
6.   while P does not meet E do
7.     R ← IdentifyRefinementRegion(P, E)
8.     RefineRegion(G, $v_0$, $v_f$, R)
9.     P ← ShortestPath(G, $v_0$, $v_f$)
10.   P, G ← Smooth(P, E, δ)
11.   end while
12.   P, G ← Smooth(P, E, δ)
13. end for
14. P ← IPRBatching(G)
15. return Stage(P, l)

B. Sub-Algorithm Design

Algorithm 1 is modular in that different implementations of the algorithm's sub-algorithms will give different behavior. Presented herein are specific implementations of each module that have proved successful for the given task.

B1. Pre-Apply IPR (22)

In one embodiment using IPR, two methods are possible for pre-applying IPR. In the first method, the modifications described by the IPR planes and amounts are applied to the tooth geometry upfront, and this tooth geometry is used for the duration of the trajectory refinement. Alternatively, IPR-aware evaluation methods may be used during the trajectory refinement process. These evaluation methods can correctly evaluate states that describe not only tooth positions and rotations but mesial and distal IPR amounts (the "IPR configuration" portion of the state). In this case, the IPR configuration of the setup state is copied over the IPR configuration of the maloccluded state. The methods will produce identical behavior.

B2. Multi-Resolution Trajectory Refinement

The algorithm performs refinement of the path P at multiple resolutions, beginning at low resolution (large δ) and subsequently moving to higher resolutions (small δ). In the preferred mode, the algorithm uses the following array of δs: [8.0, 4.0, 2.0, 1.0]. Each step of multi-resolution adjustment is discussed individually below.

B2a. Resolution Adjustment (26)

This step modifies a path in a graph to enforce a given resolution. Algorithm 2 describes the implementation.

---
Algorithm 2 AdjustResolution(G, P, δ)
---

Input: A graph G.
Input: A path P ∈ G.
Input: A stepsize δ.
Output: A new path P' that follows P at resolution δ. G is also updated to resolution δ along P.
1:   P' ← $p_1$.
2:   for $p_i$ ∈ $p_2$ ... $p_n$ do
3:     I ← Interpolate($p_{i-1}$, $p_i$, δ).

-continued

---
Algorithm 2 AdjustResolution(G, P, δ)
---

4:     Append I to P'.
5:     Remove the edge ($p_{i-1}$, $p_i$) from G. Add I to G with its corresponding edges.
6:   end for
7:   return P'.

This algorithm 2 uses an interpolate subroutine with two options: same finish where all teeth complete their motion at the same (last) stage; and fast finish where teeth complete their motion as fast as possible and may not all finish at the same stage. The preferred mode uses same finish.

B2b. Refinement Region Identification (32)

This identifies a subset of the trajectory P that needs further refinement according to some evaluation criteria E.

Some options for the output of this algorithm could include returning all portions of P that violate E, or the first offender in P, or the worst offender in P. The following approaches are possible implementations for this refinement:

IdRefinementRegionFirst: Returns the first location along P where the score computed using the evaluation criteria exceeds a threshold score.

IdRefinementRegionAll: Returns all locations along P where the score computed using the evaluation criteria exceeds a threshold score.

IdRefinementRegionWorst: Returns the worst offender in P, defined as the element that received the worst score using the evaluation criteria. In the case of a tie (i.e., multiple worst offenders), the last worst offender in P is returned.

IdRefinementRegionWorstAll: Returns all worst offenders in P.

IdRefinementRegionWorstNeighbors: Returns the worst offender in P and its N neighbors in P. In the case of a tie (i.e., multiple worst offenders), the last worst offender in P is returned.

The preferred mode of the system uses IdRefinementRegionAll.

Refinement region identification uses an evaluation criterion that is defined by an evaluator subroutine. Other scoring criteria, such as tooth displacement from gingiva or number of vertices of overlap between teeth in the arch, can also be used in place of or in addition to these described metrics. The preferred mode uses collision contact points count.

B2c. Region Refinement (34)

This refines a region of an input graph G. Algorithm 3 provides this approach.

---

Algorithm 3 RefineRegion(G, $v_0$, $v_f$, R)

---

Input: A graph G
Input: The initial and final setups $v_0$ and $v_f$
Input: A region in G to refine R (identified using Refinement Region Identification)
Output: G is refined near R to produce a better path in G from $v_0$ to $v_f$.
1. P ← ShortestPath(G, $v_0$, $v_f$)
2. $s_P$ ← ScorePath(P)
3. Let Candidates be the vertices in R.
4. Let Neighbors be the vertices adjacent to R.
5. while score(P) ≥ $s_P$ do
6.    c ← SelectCandidate(Candidates)
7.    c' ← IterativePerturb(c)
8.    if score(c') ≤ score(c)
9.       C ← Interpolate(c, c', δ)
10.      C_valid ← ExtractValidSubset(C)
11.      if len(C_valid) < max_length
12.         Add C_valid to G, Candidates, and Neighbors
13.         for each $c_{neigh}$ ∈ {k best scoring vertices in Neighbors} do
14.           C ← Interpolate(c', $c_{neigh}$, δ)
15.           C_valid ← ExtractValidSubset(C)
16.           Add C_valid to G, Candidates, and Neighbors
17.         end for
18.      end if
19.    end if
20.    P ← ShortestPath(G, $v_0$, $v_f$)
21.    P ← Smooth(P, E, δ)
22. end while

---

This algorithm 3 uses a SelectCandidate subroutine to identify a candidate from the list of Candidates. Two approaches have been identified for this subroutine:
1. Random selection: Chose the candidate randomly from the list of Candidates.
2. A * graph search: Select the candidate node based on the calculation of a heuristic. A heuristic is a quantity that estimates the "remaining cost" of a node (i.e., the quantified effort to travel from that node to the end state of the graph). The A * algorithm uses heuristics to efficiently search graphs, choosing the next node to explore using a heuristic to predict which node is most promising. A single node is selected for exploration from the list of Candidates using a heuristic.

The following heuristics are possible:

Euclidean distance between the candidate state and the setup state: For each candidate state, compute the Euclidean distance between all tooth positions in the candidate state and the setup state; then compute the heuristic as the sum or average of these distances; and choose the candidate node by minimizing the heuristic.

Extent of collision: The extent of collision can be quantified by counting the number of points from one tooth that lie within the bounds of another tooth, or alternatively by computing the number of contact points between two meshes. Compute the heuristic as the count of these points of overlap between teeth in the arch. The next node can be chosen by maximizing the count of collisions (in order to force early exploration of problematic states) or minimizing the count of collisions (for an algorithmic approach that attempts to solve the problem by identifying locally optimal (i.e., easy-to-resolve) nodes before progressing to more difficult-to-resolve locations).

In the preferred mode, the candidate is chosen randomly for all iterations except for the first iteration, where instead the candidate with the worst score according to a heuristic is selected. The heuristic is the number of contact points.

Additionally, Algorithm 3 uses an IterativePerturb subroutine, which iteratively perturbs the state according to a Perturb function, ultimately choosing the state c' that achieves the best score according to an evaluator. In the preferred mode, IterativePerturb is called 50 times, and the evaluator computes the number of collision points. The preferred mode uses propagated directional perturbation, which perturbs teeth that are in collision as well as and neighboring teeth in the direction roughly opposite to the directional penetration vector.

Algorithm 3 uses a ScorePath subroutine to compute $s_P$, the score of the shortest path, P, along graph G. The path score can be computed using the function:

$$s_P = \text{sum}([(\text{number of collisions at location}_i + 1)^{1.25} \text{ for location}_i \text{ in } P])$$

An ExtractValidSubset subroutine is used to extract the subset of an interpolated path, C, that is valid according to some evaluator function. The preferred mode uses number of collision points as the evaluator, considering only nodes with 0 collision points to be valid.

The preferred mode for the Smooth function is the iterative smoother described in "B2d. Trajectory smoothing" below.

B2d. Trajectory Smoothing (30, 38)

There are many possible smoothing algorithms. One possibility (Algorithm 5) attempts all possible edges between any two nodes in P, only retaining those that meet E at resolution 6·However, this approach is computationally expensive, especially for long paths. Instead, smoothing can be attempted only for nodes that are within a distance threshold of each other. Another implementation includes an iterative smoother that applies this smoothing process repeatedly until a score is no longer improved through smoothing. This iterative smoother is the preferred mode.

Algorithm 5 Smooth(P, E, δ)

Input: A sequence of setups P from $p_0$ to $p_n$.
Input: An evaluation function E that assigns scores to setups.
Input: A stepsize δ.
Output: A smoothed trajectory P' at resolution δ.
 1:   Construct a graph G from the vertices and edges given by P.
 2:   for all $p_i \in P$ do
 3:     for all $p_j \neq p_i \in P$ do
 4:       $P_{ij} \leftarrow$ Interpolate($p_i$, $p_j$, δ).
 5:       if $P_{ij}$ meets E then
 6:         Add $P_{ij}$ to G.
 7:       end if
 8:     end for
 9:   end for
10:   return ShortestPath(G, $p_0$, $p_n$).

B3. IPR Batching (40)

Because IPR was pre-applied (Section B1), automated intermediate trajectory finding is performed initially with all IPR performed up front when teeth are in the maloccluded state. However, it is often impossible or not practical to do this in practice, as teeth need to be accessible in order to perform IPR and may not become accessible until a later point during treatment. This section provides a strategy for incorporating IPR batching into planning. The method takes as input the graph and path generated by the algorithm when IPR is applied up front (the output from Section 2). This path is then refined based on IPR application.

The method for IPR incorporation is described below. First, how to determine IPR accessibility is discussed. Then, different ways to apply IPR batching for a given trajectory are provided. In other embodiments, IPR batching is not required.

B3a. IPR Accessibility

For realistic IPR application, the mesial or distal surface of the tooth must be accessible, meaning that the tooth cannot be situated behind another tooth or intersect with the labial/lingual surface of another tooth (see FIGS. 5A and 5B). IPR accessibility is thus determined by taking a weighted sum of tooth distance behind its neighboring tooth and tooth intersection with its neighboring tooth.

To measure tooth distance in front of or behind another tooth, the mesial/distal region of each tooth is identified, as represented by the shaded regions 52 of FIGS. 6A (occlusal view) and 6B (frontal view). The distance between the mesial/distal points of neighboring teeth in the direction normal to the arch form is then computed. To measure tooth intersection with its neighbor, a ray is drawn along the tooth incisal edge, and the closest intersection point with the neighboring tooth is identified. The distance between the intersection point and the mesial or distal region of the neighboring tooth is computed. The following are several other approaches of determining if a contact between two neighboring teeth is approved for IPR application: by distance along the incisal edge from the mesial/distal surface, and by outward normal orientation, and a hybrid method that combines those two ways. These approaches are discussed in turn below.

By Contact Point Projection to Incisal Edge. The algorithm defines the mesial/distal region as the area near the endpoints of the incisal edge, see the shaded regions 52 of FIGS. 6A (occlusal view) and 6B (frontal view). The incisal edge may be defined as: a line segment connecting incisal edge DSL/ABO landmarks (if landmarks are provided); and a line segment connecting the minimum and maximum tooth vertices along the tooth's local x-axis projected to the local z=0 plane (if no landmarks are provided). To determine accessibility, the contact point is first projected to the z=0 plane and then projected to the incisal edge line segment. If this projected point is within an absolute distance or distance percentage threshold to the nearest incisal edge endpoint, the point is accessible for IPR. Otherwise the point is not accessible. Likely an absolute distance would be sufficient as the maximum IPR to apply is given as input when the final setup is provided. A contact point is in the IPR region 52 if it lies nears the incisal endpoints 54, as shown in FIGS. 6A and 6B.

By Contact Point Outward Normal Orientation. The algorithm can also define the mesial/distal region as the area where outward normals are approximately oriented along the arch form (see the shaded region 56 of FIG. 7). IPR accessibility is determined by comparing the outward contact point normal to the local tooth x-axis.

Hybrid Approach. A hybrid approach combines the approaches presented above. If one approach is indeterminate, then the other approach can be used.

B3b. IPR Application

Once there is a model for determining if IPR is accessible, that model can be used to decide when IPR is possible. This allows for relaxing the assumption that IPR is always immediately applied. RefineTrajectoryWithIPR is similar to the trajectory refinement approach presented in Section B2 when only a single resolution level is used.

Algorithm 1 RefineTrajectoryWithIPR($v_0$, $v_f$, G, δ, l, E)

Input: The initial and final setups $v_0$ and $v_f$. Typically, $v_0$ is the maloccluded setup and $v_f$ is the final proposed setup. $v_0$ may not have IPR applied yet.
Input: A graph G containing vertices $v_0$ and $v_f$. $v_0$ and $v_f$ are connected in G and the shortest path between them is the result of a prior irajectory refinement where IPR was applied at the beginnning.
Input: A stepsize δ.
Input: A staging limit l.
Input: An evaluation function E that assigns scores to setups.
Output: A staged trajectory at resolution l that starts at $v_0$, ends at $v_f$, IPR applied when accessible, and minimizes undesirable motions.
 1: for all $v \neq v_f \in G$ do
 2:   Reset IPR degrees of freedom to 0 (e.g., none applied).
 3: end for
 4: P ← ShortestPath(G, $v_0$, $v_f$).
 5: P ← AdjustResolution(G, P, δ).
 6: ApplyIPR(P, G).
 7: while P does not meet E do
 8:   P ← Smooth(P, E, δ).
 9:   R ← IdentifyRefinementRegion(P, E).

| Algorithm 1 RefineTrajectoryWithIPR($v_0$, $v_f$, G, δ, l, E) |
| --- |
| 10:   RefineRegion(G, $v_0$, $v_f$, R).
11:     P ← ShortestPath(G, $v_0$, $v_f$).
12: end while
13: P ← Smooth(P, E, δ).
14: return Stage(P, l). |

First, all applied IPR is reset back to 0, except for $v_f$. Then IPR is applied to P according to an IPR strategy (see Section B3c: IPR Strategy). Refinement proceeds as before to remove any remaining invalid portions of the trajectory.

The ApplyIPR subroutine examines the path P, applying IPR up to the limits given in $v_f$ only when accessible and based on an application policy. (IPRisAccessible in Algorithms 2 and 3 implements the desired access model from Section 3a. IPR Accessibility). When IPR is applied to a particular vertex, it is propagated to all of its children (i.e., IPR values only increase along the trajectory, meaning tooth material is not added back).

B3c. IPR Strategy

The following are two possible IPR batching policies: as soon as possible and batching to minimize the number of IPR sessions.

As soon as possible: Algorithm 2 below simply iterates through P, applying the full IPR value from $v_f$ to neighboring pairs of teeth that do not have the full value yet applied and are accessible as reported by IPRisAccessible (see Section B3a. IPR Accessibility).

Thus, IPR should be fully applied when accessible. There is also a preference for applying IPR as early in treatment as possible.

To optimize for batching, the algorithm can examine when every IPR application point is accessible along P. The algorithm can use an accessibility matrix for this feature (FIG. 8). IPR application points lie along the x-axis in the matrix. Note that teeth that do not need any IPR applied (e.g., molars or teeth with the same IPR in $v_0$ as in $v_f$) are excluded from this matrix as they are not actionable IPR application points. The y-axis represents the path steps along P, going from $v_0$ to $v_f$. Each cell is shaded if that IPR application point is accessible at that path step (determined using IPRisAccessible from Section B36a). A horizontal cut, represented by lines 58 and 60, along this matrix represents applying IPR to the shaded set of teeth collectively. Thus, the algorithm seeks to minimize the number of cuts required to cover all IPR application points. For a given cut, IPR is applied at the first path step where the maximum number of teeth are accessible.

| Algorithm 2 ApplyIPR(P, G) |
| --- |
| Input: A path P from $v_0$ to $v_f$ in G.
Output: An updated path P and graph G with IPR applied as soon as possible.
  1: v ← $v_0$.
  2: while v ≠ $v_f$ do
  3:     for each neighboring pair of teeth ($t_1$, $t_2$) ∈ v do
  4:         if IPR present between $f_1$ and $f_2$ at v < IPR present between $t_1$ and $t_2$ at $v_f$
              then
  5:             if IPRisAccessible($t_1$, $t_2$) then
  6:                 Apply IPR to $t_1$ and $t_2$ with values from $v_f$.
  7:                 Propagate IPR all children of v in P and G regardless of future
                    accessibility and excluding $v_f$ (as to not override final values with a
                    partial application).
  8:             end if
  9:         end if
 10:     end for
 11:     v ← successor of v along P.
 12: end while
 13: return (P, G). |

Batching to minimize number of IPR sessions: IPR batching can be considered as an optimization problem where one wants to minimize the number of times that IPR is applied.

Algorithm 3 below outlines how this accessibility matrix may be used to apply batched IPR. In Algorithm 3, IPRisAccessible is not explicitly called before applying IPR, as it is implied in the construction of the accessibility matrix A.

| Algorithm 3 ApplyIPR(P, G) |
| --- |
| Input: A path P from $v_0$ to $v_f$ in G.
Output: An updated path P and graph G with IPR applied as soon as possible.
  1: Construct a |P| × n accessiblity matrix A, where n is the number of teeth
     pairs (i.e., IPR application points).
  2: Minimize the number of slices through A that cover all IPR application
     points. Let S contain these slices.
  3: for each s ∈ S do
  4:     for each neighboring pair of teeth ($t_1$, $t_2$) ∈ s do
  5:         Apply IPR to $t_1$ and $t_2$ with values from $v_f$. |

| Algorithm 3 ApplyIPR(P, G) |
| --- |
| 6:      Propagate IPR all children of v in P and G regardless of future accessibility and excluding $v_f$ (as to not override final values with a partial application).
7:      end for
8:  end for
9:  return (P, G). |

The key step is the minimization function for finding the slices S. To do this, the algorithm adds slices to S starting with the slice that maximizes the number of remaining application points affected.

B4. Trajectory Staging (42)

The objective of trajectory staging is to create a path P at a resolution l, which is defined based on per-stage tooth movement limits. Pseudo-code for this approach is shown below:
1. P_staged=P[0]
2. Compute Δd, the change in tooth position from mal-occluded state for each node in P
3. For each Δd:
   a. If Δd>per-stage tooth movement limits:
   b. Append P[i−1](the node immediately prior to the current node) to P_staged
   c. Recompute Δd as the change in tooth position from P[i−1]
4. Append the setup state (P[end]) to P_staged In the system, trajectory staging need not but could be used. Instead, the resolution that the system uses to interpolate the path is equal to the per-stage tooth movement limits.

B5. Treatment Re-Design (25, 27)

Digital orthodontic treatment planning follows an iterative process:
1. Manually create final setup, or evaluate and adjust an automatically generated final setup.
2. Staging: Manually create intermediate stages, or evaluate and adjust a set of automatically generated intermediate stages.
3. Send final setup and staging to practitioner for approval.
4. Make requested adjustments; if final setup is changed, re-compute step 2 Staging.
5. Repeat Steps 3-4 as necessary.

When the final setup is changed, the staging must also be adjusted to reflect the new final setup. The staging can be completely recomputed with the new adjusted final setup as the target. However, adjustments are often minor and much of the prior staging computation could potentially be reused. Embodiments of this invention include a method to reuse computation that will increase the responsiveness of the automated software for the technician. This method can improve a technician's workflow by reducing the amount of time spent waiting for staging to re-compute. This method could also reduce the amount of context switching between cases, as a technician or others may not need to move on to a new case while they wait for staging to re-compute. This method can also be used to provide interactive tools for the practitioner to compare treatment plans and educate the patient.

Approach

The idea is to create connections (edges) between the interpolation of the initial setup to the new final setup and the graph produced by a prior staging computation. This augments the solution exploration process with the prior effort. The staging process then proceeds as before. The following algorithm provides a high-level view of the intermediate staging process with precomputed-graph-reuse incorporated. Based upon Algorithm 1 in Section A, additions to support computation reuse are in steps 1, 4, and 5, along with additional inputs.

| Algorithm: RefineTrajectory(v0, vf, G, d, l, E, G0) |
| --- |
| Input: The initial and final setups v0 and vf
Input: A graph G containing vertices v0 and vf, where v0 and vf are connected in G. G may simply be a graph with only these 2 vertices and a single edge connecting them, a graph with a series of key setups informed by the case's motion rules, or a graph from a prior setup proposal search.
Input: A step size d
Input: A staging limit l
Input: An evaluation function E that assigns scores to setups
Input: A graph G0 from a previous RefineTrajectory run. G0 is null if there is no previous run.
Input: A small connection constant k.
Output: A staged trajectory at resolution l that starts at v0, ends at vf, and minimizes undesirable motions.
  1. Add G0 to G
  2. P ← ShortestPath(G, v0, vf)
  3. P ← AdjustResolution(G, P, d)
  4. For all p in P:
     Attempt the k nearest connections between p and G0.
  5. P ← ShortestPath(G, v0, vf)
  6. While P does not meet E:
     P ← Smooth(P, E, d)
     R ← IdentifyRefinementRegion(P, E)
     RefineRegion(G, v0, vf, R)
     P ← ShortestPath(G, v0, vf) |

Algorithm: RefineTrajectory(v0, vf, G, d, l, E, G0)

7. P ← Smooth(P, E, d)
8. Return Stage(P, l)

Prior to being added to G, the prior graph G0 could optionally be modified to provide an initial estimate for how the graph may need to be modified. This modification could be achieved by a scaling motion at each node for teeth that have been modified in the final setup. For each tooth that has been modified in the final setup, the motion would be scaled proportionally to the magnitude and direction of change in position.

The perturbation directions learned from the previous graph, G0, could also be stored and reused during the RefineRegion stage to motivate searching in directions that are more likely to improve the score. The stored perturbation directions could either be actual perturbation directions or related data such as gradient calculations that could be used to randomly sample or derive new perturbed states.

To connect the prior graph G0 to the new graph G, additional edges need to be added between them. It is computationally expensive (and not necessary) to attempt connections from all of G to vertices G0. Instead, only the subset of G containing the candidate path P needs to have additional connections attempted to vertices G0. For each vertex p in P, connections should be attempted to vertices in G0, which is typically done by attempting connections between p's k-nearest neighbors in G0.

The RefineRegion step contains a SelectCandidate subroutine that is used to identify a candidate from a list of Candidates. The SelectCandidate subroutine could be modified to preferentially select candidate teeth that have been changed in the final setup, as well as their neighboring teeth.

In a rare situation that the nearest neighbors in the previous graph for the nodes in the new graph are very distant (distance above a pre-determined threshold), G0 could be abandoned, and the adjustment can be treated as refine region from the start as if it were a new staging calculation. This can potentially be approximated using the distance between original final setup and the modified final setup. If this distance is too great, the additional cost of computing nearest neighbors could be avoided and the procedure can revert to doing the staging from the start.

Interactive System

Due to the computational efficiency of this algorithm, it could potentially be deployed as a dashboard that would allow a doctor or technician to visualize the effects of changing a final setup on the intermediate stages in real-time. In some other methods, a dashboard could be impractical due to the long computation time to re-compute stages; methods of this embodiment can decrease the computation time. Some information that could be displayed in this dashboard panel includes: total tooth movement per tooth; number of stages; and amount of pure extrusion or torque (i.e., movements that are difficult or impossible for an aligner to achieve).

By providing this immediate feedback, the technician and/or doctor could experiment with multiple final setup modifications to understand how modifications affect treatment time, tooth movement feasibility, and other factors, and ultimately plan desirable treatments with fewer iterations between doctors prescribing treatment and technicians designing treatment plans.

An alternative dashboard could be designed which would display the original (pre-modification) final setup, either on half a display screen, or in a smaller inset window, with key information such as that provided above, so that a technician or doctor could easily compare the effects of modifications and automatically revert to the saved, previously generated setup and staging. For example, if applying some small modifications to the final setup increases the number of stages past an amount the doctor is comfortable with, they could simply select ("click on") the inset window or a "Revert to Original" button to load back in the prior final setup and its staging without having to undo the changes they may have made. This allows a certain amount of fine-tuning the final setup. Additionally, the view of the teeth and arches in the pre-computed and in-modification stagings could be locked so that they are always moved together, allowing easier comparison.

C. Additional Components and Capabilities

C1. Multiple Path Extraction

This component enables a set of valid paths to be presented to a practitioner, enabling the practitioner or patient to select the desired treatment path. To benefit the technician or practitioner, multiple path choices should be dissimilar. In particular, they should all be viable but have different high-level properties such as number of IPR stages, amount of round-tripping, or other options. To provide this, paths should be scored or annotated based on such properties. Then the algorithm would identify all viable paths, sort them by score, and report back the best scoring paths that do not share the same properties as other, better-scoring, paths in the list.

C2. Multiple IPR Policies

This component would offer practitioners a choice of what IPR application policy to apply: as soon as possible, batching to minimize the number of treatments, or a policy in between. Options can be provided to the practitioner, who would then evaluate different options on a case by case basis if desired or if their preferred policy yields less than desirable results.

C3. Single vs. Multiple Arch

In one implementation, upper and lower arches are considered separately because it is an easier (and thus faster) problem to solve. In another embodiment, both arches are supported and considered together in the case that this is preferred, for example.

C4. Interactive Tools

Several of the library components can either be fully specified by the user, fully automated, or interactive, where the user provides inputs to the automatic method. This spectrum can be seen in the following areas.

Key Setup Generation—This can be one of the most difficult steps to automate yet the user may be able to provide inputs to the method. Selecting useful key setups could rely on the ability to classify what case type one is considering (crowding, midline correction, etc.). This is something that may be learned over time by an algorithm but is easy for a technician to provide (via quick visual inspection and an input such as a checkbox). In addition, a technician could also explicitly provide intermediate stages that characterize the corrective treatment plan for the case type.

Perturbation Motions—To a lesser degree than above, a technician may also be able to provide corrective motion planning possibly through approximate setup input. This planning can then be applied during automated perturbation of invalid states, enabling a clinically valid solution to be discovered more quickly.

Identification of Refinement Regions—If the algorithm is focused on some local minima, a user may be able to identify good regions for refinement based on visual inspection and manually perturb the state towards these good regions.

The invention claimed is:

1. A method for generating and reusing setups for an orthodontic treatment path using a system, the method comprising, comprising steps of:
   receiving a digital 3D model of teeth;
   receiving a plurality of successively increasing resolutions, wherein lower resolutions specify larger tooth movement step sizes in a treatment path and higher resolutions specify smaller tooth movement step sizes in a treatment path;
   generating an initial treatment path with stages including an initial setup, a final setup, and a plurality of intermediate setups;
   for each resolution in the plurality of successively increasing resolutions,
      dividing the initial treatment path into steps of feasible motion of the teeth within a step size specified by the resolution resulting in a modified treatment path with setups corresponding with the steps of feasible motion;
      computing new steps of feasible motion of the teeth for only a portion of the initial treatment path within the step size specified by the resolution;
      updating the initial treatment path based at least on the modified treatment path or by adding the computed new steps to the initial treatment path within the step size specified by the resolution;
   generating a final treatment path based on iteratively processing the initial treatment path at each resolution in the plurality of successively increasing resolutions; and
   manufacturing one or more orthodontic aligners using a 3D printer coupled to the system, based on a final digital setup corresponding to the final treatment path.

2. The method of claim 1, wherein the generating the initial treatment path step comprises generating the initial treatment path with key intermediate setups.

3. The method of claim 1, wherein the dividing step further comprises generating one or more evaluation criteria that assigns scores to the setups and dividing the treatment path is based, at least in part on, the evaluation criteria.

4. The method of claim 3, wherein if the treatment path does not satisfy the evaluation criteria, generating a new treatment path.

5. The method of claim 4, wherein the generating the new treatment path comprises applying a smoothing algorithm to the treatment path.

6. The method of claim 4, wherein the generating the new treatment path comprises applying a region refinement algorithm to the treatment path.

7. The method of claim 4, wherein the generating the new treatment path comprises finding a shortest treatment path that satisfies the evaluation criteria.

8. The method of claim 1, wherein the dividing step comprises dividing the final treatment path based upon key frames.

9. The method of claim 1, wherein the dividing step comprises generating multiple final treatment paths.

10. The method of claim 9, further comprising reporting one or more scores for each of the multiple treatment paths.

11. The method of claim 9, further comprising selecting the final treatment path among the multiple final treatment paths based upon user input.

12. The method of claim 1, further comprising:
   performing interproximal reduction (IPR) on the digital 3D model;
   computing IPR accessibility for each tooth at each stage of the initial treatment path; and
   applying IPR throughout the initial treatment path based upon the computed IPR accessibility.

13. The method of claim 12, wherein the applying step comprises applying an IPR batching algorithm to the treatment path.

14. A system configured to generate and reuse setups for an orthodontic treatment path, comprising:
   one or more computer processors; and
   non-transitory computer-readable storage communicatively coupled with the one or more computer processors and having instructions stored thereon that when executed cause the one or more computer processors to:
      receive a digital 3D model of teeth;
      receive a plurality of successively increasing resolutions, wherein lower resolutions specify larger tooth movement step sizes in a treatment path and higher resolutions specify smaller tooth movement step sizes in a treatment path;
      generate an initial treatment path with stages including an initial setup, a final setup, and a plurality of intermediate setups;
      for each resolution in the plurality of successively increasing resolutions,
         divide the initial treatment path into steps of feasible motion of the teeth within a step size specified by the resolution resulting in a modified treatment path with setups corresponding with the steps of feasible motion;
         compute new steps of feasible motion of the teeth for only a portion of the initial treatment path within the step size specified by the resolution;
         update the initial treatment path based at least on the modified treatment path or by adding the computed new steps to the initial treatment path within the step size specified by the resolution;
      generate a final treatment path based on iteratively processing the initial treatment path at each resolution in the plurality of successively increasing resolutions; and
      manufacture one or more orthodontic aligners using a 3D printer coupled to the system, based on a final digital setup corresponding to the final treatment path.

15. The system of claim 14, wherein the instructions further cause the one or more processors to:
   perform interproximal reduction (IPR) on the digital 3D model;
   compute IPR accessibility for each tooth at each stage of the initial treatment path; and
   apply IPR throughout the initial treatment path based upon the computed IPR accessibility.

16. The system of claim 15, wherein the applying step comprises applying an IPR batching algorithm to the treatment path.

\* \* \* \* \*